United States Patent [19]

Freskos

[11] Patent Number: 4,929,723
[45] Date of Patent: May 29, 1990

[54] PROCESS FOR PREPARING 2-DEOXYNUCLEOSIDES

[75] Inventor: John N. Freskos, Baton Rouge, La.

[73] Assignee: Ethyl Corporation, Richmond, Va.

[21] Appl. No.: 341,428

[22] Filed: Apr. 21, 1989

Related U.S. Application Data

[63] Continuation of Ser. No. 76,100, Jul. 21, 1987, abandoned.

[51] Int. Cl.$^5$ .................. C07H 19/073; C07H 19/173
[52] U.S. Cl. .......................................... 536/23; 536/24
[58] Field of Search .......................................... 536/23

[56] References Cited

U.S. PATENT DOCUMENTS 3,748,320 7/1973 Vorbrüggen et al. ................. 536/23
4,121,037 10/1978 Nakamura et al. ................. 544/313

OTHER PUBLICATIONS

Nehring et al., *Agnew Chem* 82: 449 (1970).
Niedballa et al., J. of Org. Chem. 39, pp. 3654–3660 (1974).
Morrison et al., *Organic Chemistry*, Fourth Edition, Allyn and Bacon, Inc.; Boston, 1983, p. 1088.
Moore, Walter J., *Physical Chemistry*, Third Edition, Prentice-Hall, Inc.; Englewood Cliffs, N.J. 1962, pp. 309–311.

*Primary Examiner*—Johnnie R. Brown
*Assistant Examiner*—Gary L. Kunz
*Attorney, Agent, or Firm*—Patricia J. Hogan

[57] ABSTRACT

An O-, S-, or N-silyl- or O-, S-, or N-alkylpyrimidine is reacted with a protected 1-halo-, 1-alkoxy-, or 1-acyloxy-2-deoxy sugar in the presence of cuprous iodide and a halohydrocarbon solvent to prepare a nucleoside having an improved beta-anomer/alpha-anomer ratio. In a preferred embodiment of the invention, 2,4-bis(trimethylsilyloxy)-5-methylpyrimidine or 2,4-bis(-trimethylsilyloxy)-5-ethylpyrimidine is reacted with 2-deoxy-3,5-di-O-p-toluyl-D-erythro-ribofuranosyl chloride in the presence of cuprous iodide and chloroform.

13 Claims, No Drawings

PROCESS FOR PREPARING 2-DEOXYNUCLEOSIDES

This application is a continuation of application Ser. No. 076,100, filed July 21, 1987 now abandoned.

FIELD OF THE INVENTION

This invention relates to pyrimidine 2-deoxynucleosides and more particularly to a process for preparing them.

BACKGROUND

As disclosed in U.S. Pat. No. 3,748,320 (Vorbrüggen et al., it is known that pyrimidine nucleosides are useful in the pharmaceutical industry and that they can be prepared by reacting a suitable pyrimidine with a protected 1-halo, 1-alkoxy, or 1-acyloxy sugar in the presence of tin tetrachloride, titanium tetrachloride, zinc chloride, boron trifluoride, aluminum chloride, or ferric chloride as a catalyst. This process has been found to be very satisfactory for preparing biologically-active nucleosides from sugars having a 2-hydroxy group. However, it is less satisfactory for preparing nucleosides from 2-deoxy sugars. When a 2-deoxy sugar derivative is used as a starting material in the process of Vorbrüggen et al., the amount of the biologicallyinactive alpha-anomer formed is substantial, and the yield of the desired beta-anomer is accordingly decreased. In fact, it appears that the best beta-anomer/alpha-anomer ratio that can be obtained when a 2-deoxy sugar derivative is used in the process is only about 60/40. It would be advantageous to be able to increase this ratio.

SUMMARY OF THE INVENTION

An object of this invention is to provide a novel process for preparing pyrimidine 2-deoxynucleosides.

Another object is to provide such a process characterized by improved selectivity to the beta-anomer.

These and other objects are attained by reacting an O-, S-, or N-silyl- or O-, S-, or N-alkylpyrimidine with a protected 1-halo-, 1-alkoxy-, or 1-acyloxy-2-deoxy sugar in the presence of a halohydrocarbon solvent and cuprous iodide as a catalyst.

DETAILED DESCRIPTION

Except for the cuprous iodide catalyst, the materials employed in the process of the invention are basically the same as materials that can be used in the 2-deoxynucleoside syntheses of Vorbrüggen et al., the teachings of which are incorporated herein in toto by reference.

Thus, pyrimidines that can be used in the process are generally compounds corresponding to the formula:

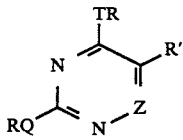

in which Q is oxygen or sulfur; R is alkyl or trialkylsilyl; R' is hydrogen or an inert substituent; T is oxygen or —NR" wherein R" is hydrogen, alkyl, aryl, or aralkyl; and Z is CH or N. When R' is an inert substituent, it may be any substituent which is inert under the reaction conditions, but it is most commonly alkyl (preferably methyl, ethyl, or other alkyl of 1–10 carbons most preferably 1–4 carbons), alkoxy (preferably methoxy, ethoxy or other alkoxy of 1–10 carbons, most preferably 1–4 carbons) chloro, bromo, fluoro, iodo, nitro, cyano, trifluoromethyl, bromovinyl, acetyl, or the like. The alkyl groups in R and any alkyl in R" are preferably alkyl groups containing 1–10 carbons, most preferably 1–4 carbons. When R" is aryl, it may be, e.g., phenyl tolyl, ethylphenyl, naphthyl, etc.; when it is aralkyl, it may benzyl, phenethyl, etc.

Exemplary of the utilizable pyrimidines are:
2,4-bis(trimethylsilyloxy)pyrimidine,
2,4-bis(trimethylsilyloxy)-5-methylpyrimidine,
2,4-bis(trimethylsilyloxy)-5-ethylpyrimidine,
2,4-bis(trimethylsilyloxy)-5-trifluoromethyl-pyrimidine,
2,4-bis(trimethylsilyloxy)-5-fluoropyrimidine,
2,4-bis(trimethylsilyloxy)-5-iodopyrimidine,
2,4-bis(trimethylsilyloxy)-5-nitropyrimidine,
2,4-bis(trimethylsilyloxy)-6-azapyrimidine,
2,4-bis(trimethylsilyloxy)-6-aza-5-methylpyrimidine,
2-trimethylsilylthio-4-trimethylsilyloxypyrimidine,
2-trimethylsilylthio-4-trimethylsilyloxy-5-carboxyethylpyrimidine,
2-trimethylsilylthio-4-trimethylsilyloxy-5-ethoxypyrimidine,
2-trimethylsilylthio-4-trimethylsilyloxy-5-propylpyrimidine,
2-trimethylsilyloxy-4-trimethylsilylaminopyrimidine,
2-trimethylsilyloxy-4-trimethylsilylamino-5-fluoropyrimidine,
2-trimethylsilyloxy-4-trimethylsilylmethylaminopyrimidine,
2-trimethylsilyloxy-4-trimethylsilylbenzylaminopyrimidine,
2-trimethylsilyloxy-4-trimethylsilylphenylaminopyrimidine,
2-trimethylsilylthio-4-trimethylsilylmethylaminopyrimidine,
2-trimethylsilylthio-4-trimethylsilylamino-5-cyanopyrimidine,
2,4-bis(triethylsilyloxy)pyrimidine,
2-trimethylsilyloxy-4-dimethylaminopyrimidine,
2,4-dimethoxy-5-iodopyrimidine, etc.
The preferred pyrimidines are the bis-trimethylsilyl ethers especially when freshly prepared.

The protected sugar derivative that is reacted with the pyrimidine is a compound in which the sugar moiety may be any 2-deoxy sugar, e.g., a 2-deoxyribose, 2-deoxyarabinose, 2-deoxyglucose, 2-deoxyallose, 2-deoxyfructose, 2-deoxygalactose 2-deoxymannose, 2-deoxyrhamnose, 2-deoxysorbose, 2-deoxyxylose etc. However, it is preferably a compound in which the sugar moiety is a 2-deoxypentose, especially a 2-deoxyribose, most preferably a D-isomer. The sugar may be protected, i.e., have its free hydroxy groups blocked, with any of the blocking groups conventionally employed in sugar chemistry; but it is most commonly protected with acetyl, benzoyl, p-chlorobenzoyl, p-nitrobenzoyl p-toluyl, or benzyl groups.

The substituent on the 1-position of the sugar may be halo (i.e., chloro, bromo, fluoro, or iodo), alkoxy (most commonly methoxy, ethoxy, or other alkoxy group of 1–10 carbons, preferably 1–4 carbons), or acyloxy (most commonly acetyl, benzoyl, p-chlorobenzoyl, p-nitrobenzoyl, p-toluyl, or other acyl group derived from an aliphatic or aromatic carboxylic acid).

However, it is preferably halo, most preferably chloro. A protected sugar derivative that is frequently preferred for use in the process is 2-deoxy-3,5-di-O-p- toluyl-D-erythro-ribofuranosyl chloride. Exemplary of other utilizable reactants are 2-deoxy-3,5-di-O-p-nitrobenzoylribofuranosyl chloride, 2-deoxy-3,5-di-O-p-chlorobenzoylribofuranosyl chloride, 2-deoxy-3,5-di-O-benzoylribofuranosyl chloride, 2-deoxy-1-O-methyl-3,5-di-O-p-toluylribofuranose, etc.

In contrast to the process of Vorbrüggen et al., the present process is one in which the choice of solvent is critical. The solvent must have a low dielectric constant in order for the selectivity to beta-anomer to be increased. Thus, the solvent should be a halohydrocarbon, such as methylene chloride, chloroform, carbon tetrachloride, dichloroethane, tetrachloroethane, chlorobenzene, the corresponding bromohydrocarbons, etc. A particularly preferred solvent is chloroform.

The catalyst employed in the process is cuprous iodide, which is unique in its ability to improve the selectivity to the beta-anomer. Neither the Lewis acids of Vorbrüggen et al. nor other Lewis acids, such as cuprous bromide, cuprous chloride, cupric sulfate, magnesium sulfate, zinc iodide, aluminum iodide, etc., are equivalent to cuprous iodide in this regard.

The reaction is conveniently conducted at room temperature, although higher temperatures, e.g., temperatures up to about 150° C., are sometimes desirable to speed the reaction. The reactants and catalyst are generally employed in approximately equivalent amounts, with the pyrimidine preferably being used in a slight excess, e.g., about 1.1–1.3 equivalents, to provide optimum yields. The amount of catalyst used can be as little as 0.2 equivalent, and there does not appear to be any maximum amount that can be utilized. However, yields and reaction times are improved as the catalyst concentration is increased from 0.2 to one equivalent, and there is not much improvement obtained by increasing the concentration further.

The invention is advantageous as a means of providing high yields of pyrimidine nucleosides characterized by a higher beta-anomer/alpha-anomer ratio than is obtained with conventional Lewis acid catalysts. The process also has the advantage of using a catalyst which, being insoluble in the reaction mixture, can be recovered by filtration and recycled.

The following examples are given to illustrate the invention and are not intended as a limitation thereof.

EXAMPLE I

3',5'-di-p-toluylthymidine

A suitable reaction vessel was charged with 2.62g of 2-deoxy-3,5-di-O-p-toluyl-D-erythro-ribofuranosyl chloride and 2.1 g (1.2 equivalents) of 2,4-bis(trimethylsilyloxy)-5-methylpyrimidine in 150 mL of dry dichloroethane. To this was added 1.3 g (1.0 equivalent) of cuprous iodide, and the slurry was stirred for four hours at room temperature and then heated to reflux for one hour. TLC showed no starting sugar. The reaction was quenched by the addition of 80 mL of 5% aqueous sodium bicarbonate and filtered through Celite. The organic phase was separated, washed with 50 mL of saturated bicarbonate and 75 mL of brine, dried, and concentrated in vacuo to 2.95 g (92%) of a white solid which NMR showed to be a mixture of the desired beta-product and the alpha-anomer in a ratio of 76/24. The crude solid was slurried and ground in 40 mL of absolute ethanol, filtered, and washed with 2×15 mL of additional ethanol to yield 1.77 g (58%) of product, a white solid having a melting point of 194°–195.5° C.

EXAMPLE II

3',5'-di-p-toluyl-2'-deoxyuridine

A suitable reaction vessel was charged with one gram of 2-deoxy-3,5-di-O-p-toluyl-D-erythro-ribofuranosyl chloride, 800 mg (1.2 equivalents) of 2,4-bis(trimethylsilyloxy)pyrimidine, and 500 mg (1.0 equivalent) of cuprous iodide in 80 mL of dichloroethane. The reaction was stirred at room temperature for four hours and then at reflux for one hour. The reaction was quenched and worked up as in Example I to yield 1.07 g (89%) of a white solid which NMR showed to be a mixture of the desired betaproduct and the alpha-anomer in a ratio of 74/26. The crude solid was slurried in 35 mL of ethanol, filtered, and washed with 2×15 mL of additional ethanol to yield 625 mg (53%) of the product which has a melting point of 208°–210° C.

EXAMPLE III

3',5'-di-p-toluyl-6-azathymidine

A suitable reaction vessel was charged with 500 mg of 2-deoxy-3,5-di-O-p-toluyl-D-erythro-ribofuranosyl chloride, 405 mg (1.2 equivalents) of 2,4-bis(trimethylsilyloxy)-5-methyl-6-azapyrimidine, and 260 mg (1.2 equivalents) of cuprous iodide in 60 mL of dry dichloroethane. The reaction was stirred at room temperature for four hours, then refluxed for 30 minutes, and worked up as in Example I to give 530 mg (87%) of a solid which NMR showed to be a mixture of the desired beta-product and the alphaanomer in a ratio of 84/16. The crude solid was slurried in 20 mL of ethanol to give 300 mg (49%) of product, a white solid having a melting point of 169°–171° C.

EXAMPLE IV

3',5'-di-p-toluyl-2'-deoxy-6-azauridine

A suitable reaction vessel was charged with 530 mg of 2-deoxy-3,5-di-O-p-toluyl-D-erythro-ribofuranosyl chloride, 400 mg (1.2 equivalents) of 2,4-bis(trimethylsilyloxy)-6-azapyrimidine 260 mg (1.0 equivalent) of cuprous iodide, and 65 mL of dry dichloroethane. After four hours at room temperature, the reaction was heated to reflux for 40 minutes, quenched, and worked up as in Example I to give 570 mg (90%) of an off-white foam which NMR showed to be the desired beta-product and the alpha-anomer in a ratio of 78/22. The crude product was dissolved in 15 mL of ethanol, cooled to −10° C. for two hours, and filtered to give 50 mg of a solid having a melting point of 165°–168° C. and a beta anomer/alpha-anomer ratio of 93/7.

EXAMPLE V

3',5'-di-p-toluylthymidine

A suitable reaction vessel was charged with 1.2 g (3.1 millimols) of 2-deoxy-3,5-di-O-p-toluyl-D-erythro-ribofuranosyl chloride, 1.0 g (3.4 millimols) of 2,4-bis(-trimethylsilyloxy)-5-methylpyrimidine, and 0.65 g (3.4 millimols) of cuprous iodide in 90 mL of dry chloroform. The slurry was stirred for two hours at room temperature and quenched with 60 mL of saturated sodium bicarbonate. The reaction mixture was filtered through Celite. After separation of the layers, the aqueous layer was washed with 80 mL of methylene chloride; and the combined organic layers were washed with 50 mL of saturated bicarbonate and 50 mL of brine dried over sodium sulfate, and concentrated in vacuo to 1.36 g (92%) of a white solid which NMR showed to be a mixture of the desired beta-product and the alpha-anomer in a ratio of 93/7. The crude solid was slurried in 40 mL of ethanol, filtered, and washed with 2×15 mL of additional ethanol to give 1.05 g (71%) of product, a white solid having a melting point of 195°–196° C.

EXAMPLE VI

3',5'-di-p-toluyl-2'-deoxy-5-ethyluridine

A suitable reaction vessel was charged with 1.15 g (2.9 millimols) of 2-deoxy-3,5-di-O-p-toluyl-D-erythro-ribofuranosyl chloride, 1.04 g (3.6 millimols) of 2,4-bis(trimethylsilyloxy)-5-ethylpyrimidine, and 700 mg (3.6 millimols) of cuprous iodide in 70 mL of dry chloroform. The reaction mixture was stirred for 1.5 hours at room temperature under nitrogen, quenched with 50 mL of saturated bicarbonate, and filtered through Celite. After separation of the layers, the aqueous layer was washed with 60 mL of methylene chloride; and the combined organic layers were washed with 60 mL of brine, dried over sodium sulfate, and concentrated in vacuo to 1.2 g (88%) of a white solid which NMR showed to be a mixture of the desired beta-product and the alpha-anomer in a ratio of 93/7. The crude solid was slurried with 45 mL of ethanol and filtered to yield 930 mg (68%) of product, a white solid having a melting point of 192°–194° C.

EXAMPLE VII

3',5'-di-p-toluyl-2'-deoxyuridine

A suitable reaction vessel was charged with 120 mg of 2-deoxy-3,5-di-O-p-toluyl-D-erythro-ribofuranosyl chloride, 105 mg of 2,4-bis(trimethylsilyloxy)pyrimidine, and 90 mg of cuprous iodide in 20 mL of dry chloroform. The reaction was stirred for 2.5 hours at room temperature and worked up as in Example VI to give 127 mg (92%) of a solid which NMR showed to be a mixture of the desired beta-product and the alpha-anomer in a ratio of 92/8. The crude solid was slurried in 15–20 mL of ethanol and filtered to give 98 mg (70%) of product, a white solid having a melting point of 209°–210° C.

EXAMPLE VIII

3',5'-di-p-toluyl-6-azathymidine

A suitable reaction vessel was charged with 210 mg of 2-deoxy-3,5-di-O-p-toluyl-D-erythro-ribofuranosyl chloride, 185 mg of 2,4-bis(trimethylsilyloxy)-5-methyl-6-azapyrimidine, 105 mg of cuprous iodide, and 20 mL of dry chloroform. The reaction was stirred at room temperature for 1.5 hours and worked up as in Example VI to give 230 mg (92%) of an off-white solid which NMR showed to be a mixture of the desired beta-product and the alphaanomer in a ratio of 97/3.

It is obvious that many variations may be made in the product and processes set forth above without departing from the spirit and scope of this invention.

What is claimed is:

1. In a process for preparing a nucleoside by reacting an O-, S-, or N-silyl- or O-, S-, or N-alkylpyrimidine with a protected 1-halo-, 1-alkoxy-, or 1-acyloxy-2-deoxy sugar in the presence of a Lewis acid catalyst and a halohydrocarbon solvent, the improvement which comprises increasing the beta-anomer selectivity by employing cuprous iodide as the Lewis acid.

2. The process of claim 1 wherein the pyrimidine is a compound corresponding to the formula:

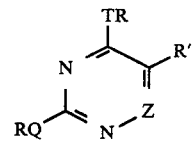

in which Q is oxygen or sulfur; R is alkyl or trialkylsilyl; R' is hydrogen, alkyl, alkoxy, chloro, bromo, fluoro, iodo, nitro, cyano, trifluoromethyl, bromovinyl, or acetyl; T is oxygen or —NR'' wherein R'' is hydrogen, alkyl, aryl, or aralkyl; and Z is CH or N.

3. The process of claim 2 wherein R is a trialkylsilyl group in which the alkyl groups contain 1–4 carbons.

4. The process of claim 3 wherein R is trimethylsilyl.

5. The process of claim 2 wherein Q and T are oxygen and R is trimethylsilyl.

6. The process of claim 2 wherein the pyrimidine is 2,4-bis(trimethylsilyloxy)-5-methylpyrimidine.

7. The process of claim 2 wherein the pyrimidine is 2,4-bis(trimethylsilyloxy)-5-ethylpyrimidine.

8. The process of claim 1 wherein the protected sugar is a protected 1-halo-2-deoxy sugar in which the free hydroxy groups are blocked with acetyl, benzoyl, p-chlorobenzoyl, p-nitrobenzoyl, p-toluyl, or benzyl groups.

9. The process of claim 8 wherein the protected sugar is 2-deoxy-3,5-di-O-p-toluyl-D-erythro-ribofuranosyl chloride.

10. The process of claim 1 wherein the halohydrocarbon is chloroform.

11. In a process for preparing a nucleoside by reacting a pyrimidine corresponding to the formula:

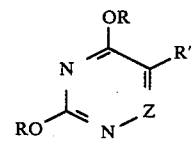

wherein R is trimethylsilyl, R' is hydrogen, alkyl, alkoxy, chloro, bromo, fluoro, iodo, nitro, cyano, trifluoromethyl, bromovinyl, or acetyl, and Z is CH or N, with a protected 1-halo-2-deoxy sugar in which the free hydroxy groups are blocked with acetyl, benzoyl, p-chlorobenzoyl, p-nitrobenzoyl, p-toluyl, or benzyl groups in the presence of a Lewis acid catalyst and a halohydrocarbon solvent, the improvement which comprises increasing the beta-anomer selectivity by employing cuprous iodide as the Lewis acid.

12. The process of claim 11 wherein the pyrimidine is 2,4-bis(trimethylsilyloxy)-5-methylpyrimidine, the protected sugar is 2-deoxy-3,5-di-O-p-toluyl-D-erythro-ribofuranosyl chloride, and the halohydrocarbon is chloroform.

13. The process of claim 11 wherein the pyrimidine is 2,4-bis(trimethylsilyloxy)-5-ethylpyrimidine, the protected sugar is 2-deoxy-3,5-di-O-p-toluyl-D-erythro-ribofuranosyl chloride, and the halohydrocarbon is chloroform.

* * * * *